United States Patent [19]
Limon et al.

[11] Patent Number: 6,077,295
[45] Date of Patent: *Jun. 20, 2000

[54] SELF-EXPANDING STENT DELIVERY SYSTEM

[75] Inventors: Timothy A. Limon, Cupertino; Richard J. Saunders, Redwood City, both of Calif.

[73] Assignee: Advanced Cardiovascular Systems, Inc., Santa Clara, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/680,429

[22] Filed: Jul. 15, 1996

[51] Int. Cl.⁷ ...................................................... A61F 2/06
[52] U.S. Cl. .............................. 623/1; 606/108; 606/192
[58] Field of Search ....................... 606/1, 108, 191–200; 623/1, 11, 12

[56] References Cited

U.S. PATENT DOCUMENTS

| | | |
|---|---|---|
| 4,300,244 | 11/1981 | Bokros . |
| 4,512,338 | 4/1985 | Balko et al. . |
| 4,580,568 | 4/1986 | Gianturco . |
| 4,655,771 | 4/1987 | Wallsten . |
| 4,740,207 | 4/1988 | Kreamer . |
| 4,762,128 | 8/1988 | Rosenbluth . |
| 4,795,458 | 1/1989 | Regan . |
| 4,830,003 | 5/1989 | Wolff et al. . |
| 4,878,906 | 11/1989 | Lindemann et al. . |
| 4,886,062 | 12/1989 | Wiktor . |
| 4,893,623 | 1/1990 | Rosenbluth . |
| 4,907,336 | 3/1990 | Gianturco . |
| 4,913,141 | 4/1990 | Hillstead . |
| 4,950,227 | 8/1990 | Savin et al. . |
| 4,969,458 | 11/1990 | Wiktor . |
| 4,969,890 | 11/1990 | Sugita et al. . |
| 4,990,155 | 2/1991 | Wilkoff . |
| 4,998,539 | 3/1991 | Delsanti . |
| 5,002,560 | 3/1991 | Machold et al. . |
| 5,026,377 | 6/1991 | Burton et al. . |
| 5,034,001 | 7/1991 | Garrison et al. . |
| 5,035,706 | 7/1991 | Gianturco et al. . |
| 5,037,392 | 8/1991 | Hillstead . |
| 5,037,427 | 8/1991 | Harada et al. . |
| 5,041,126 | 8/1991 | Gianturco . |
| 5,059,166 | 10/1991 | Fischell et al. . |
| 5,061,275 | 10/1991 | Wallsten et al. . |
| 5,064,435 | 11/1991 | Porter . |
| 5,071,407 | 12/1991 | Termin et al. . |
| 5,078,720 | 1/1992 | Burton et al. . |
| 5,089,005 | 2/1992 | Harada . |
| 5,089,006 | 2/1992 | Stiles . |
| 5,092,877 | 3/1992 | Pinchuk . |
| 5,108,416 | 4/1992 | Ryan et al. . |
| 5,123,917 | 6/1992 | Lee . |
| 5,135,517 | 8/1992 | McCoy . |
| 5,158,548 | 10/1992 | Lau et al. . |
| 5,163,952 | 11/1992 | Froix . |
| 5,163,958 | 11/1992 | Pinchuk . |
| 5,171,262 | 12/1992 | MacGregor . |
| 5,183,085 | 2/1993 | Timmermans . |

(List continued on next page.)

FOREIGN PATENT DOCUMENTS

| | | |
|---|---|---|
| 2102019 | 5/1994 | Canada . |
| 0 556 940 | 8/1993 | European Pat. Off. . |
| 0 596 145 | 5/1994 | European Pat. Off. . |
| 90 10 130 U | 9/1990 | Germany . |
| WO 95/33422 | 12/1995 | WIPO . |
| WO 96/39998 | 12/1996 | WIPO . |

*Primary Examiner*—Glenn K. Dawson
*Attorney, Agent, or Firm*—Fulwider Patton Lee & Utecht, LLP

[57] ABSTRACT

A stent-delivery catheter system delivers and implants a self-expanding stent intraluminally into a human patient's body lumen. A self-expanding stent is removabaly attached to the distal end of an inner member so that attachment projections prevent axial movement of the stent on the inner member while the stent is being delivered and implanted in a patient's body lumen.

13 Claims, 6 Drawing Sheets

U.S. PATENT DOCUMENTS

| | | |
|---|---|---|
| 5,192,297 | 3/1993 | Hull . |
| 5,197,978 | 3/1993 | Hess . |
| 5,222,969 | 6/1993 | Gillis . |
| 5,222,971 | 6/1993 | Willard et al. . |
| 5,226,913 | 7/1993 | Pinchuk . |
| 5,242,451 | 9/1993 | Harada et al. . |
| 5,256,146 | 10/1993 | Ensminger et al. . |
| 5,258,020 | 11/1993 | Froix . |
| 5,263,964 | 11/1993 | Purdy . |
| 5,282,823 | 2/1994 | Schwartz et al. . |
| 5,282,824 | 2/1994 | Gianturco . |
| 5,304,200 | 4/1994 | Spaulding . |
| 5,306,294 | 4/1994 | Winston et al. . |
| 5,354,308 | 10/1994 | Simon et al. . |
| 5,354,309 | 10/1994 | Schnepp-Pesch et al. . |
| 5,372,600 | 12/1994 | Beyar et al. . |
| 5,378,239 | 1/1995 | Termin et al. . |
| 5,395,390 | 3/1995 | Simon et al. . |
| 5,403,341 | 4/1995 | Solar . |
| 5,405,377 | 4/1995 | Cragg . |
| 5,411,507 | 5/1995 | Heckele . |
| 5,415,664 | 5/1995 | Pinchuk . |
| 5,443,496 | 8/1995 | Schwartz et al. . |
| 5,453,090 | 9/1995 | Martinez et al. . |
| 5,456,694 | 10/1995 | Marin et al. . |
| 5,478,349 | 12/1995 | Nicholas . |
| 5,484,444 | 1/1996 | Braunschweiler et al. . |
| 5,496,277 | 3/1996 | Termin et al. . |
| 5,522,883 | 6/1996 | Slater et al. . |
| 5,534,007 | 7/1996 | St. Germain et al. . |
| 5,554,181 | 9/1996 | Das . |
| 5,690,643 | 11/1997 | Wijay ................................ 606/108 |
| 5,935,135 | 8/1999 | Bramfitt et al. ..................... 606/108 |

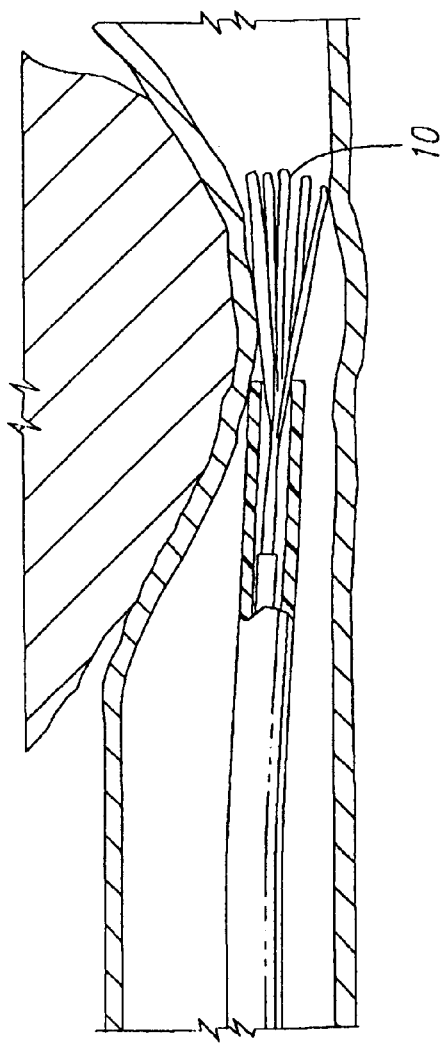
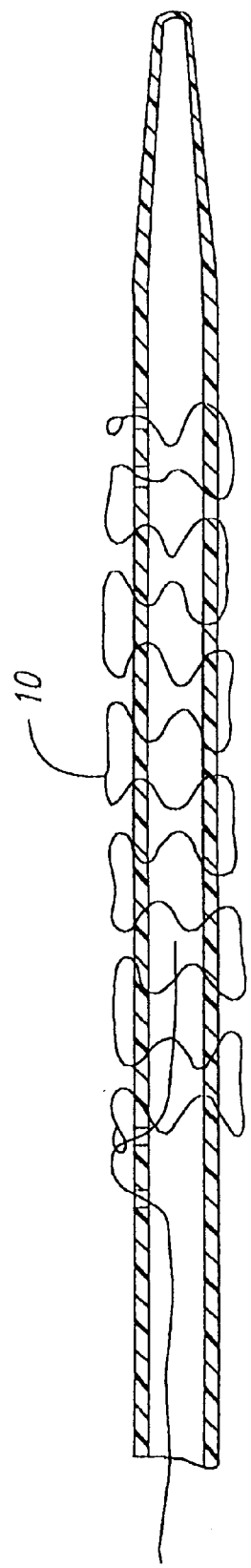
FIG. 3 PRIOR ART
FIG. 4 PRIOR ART

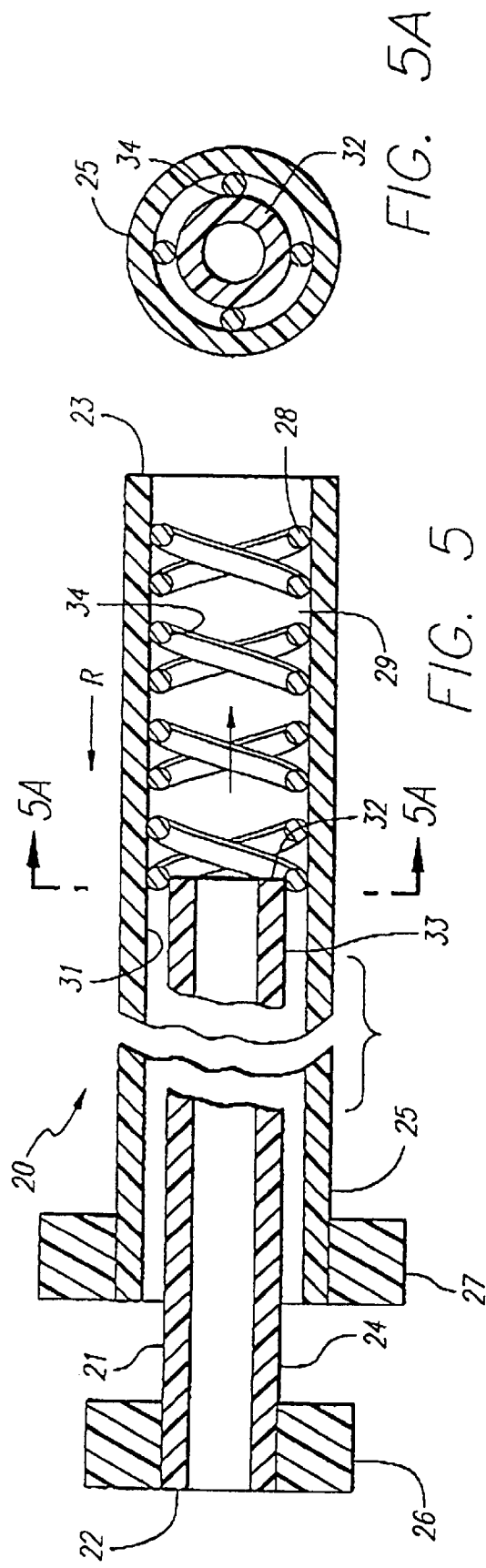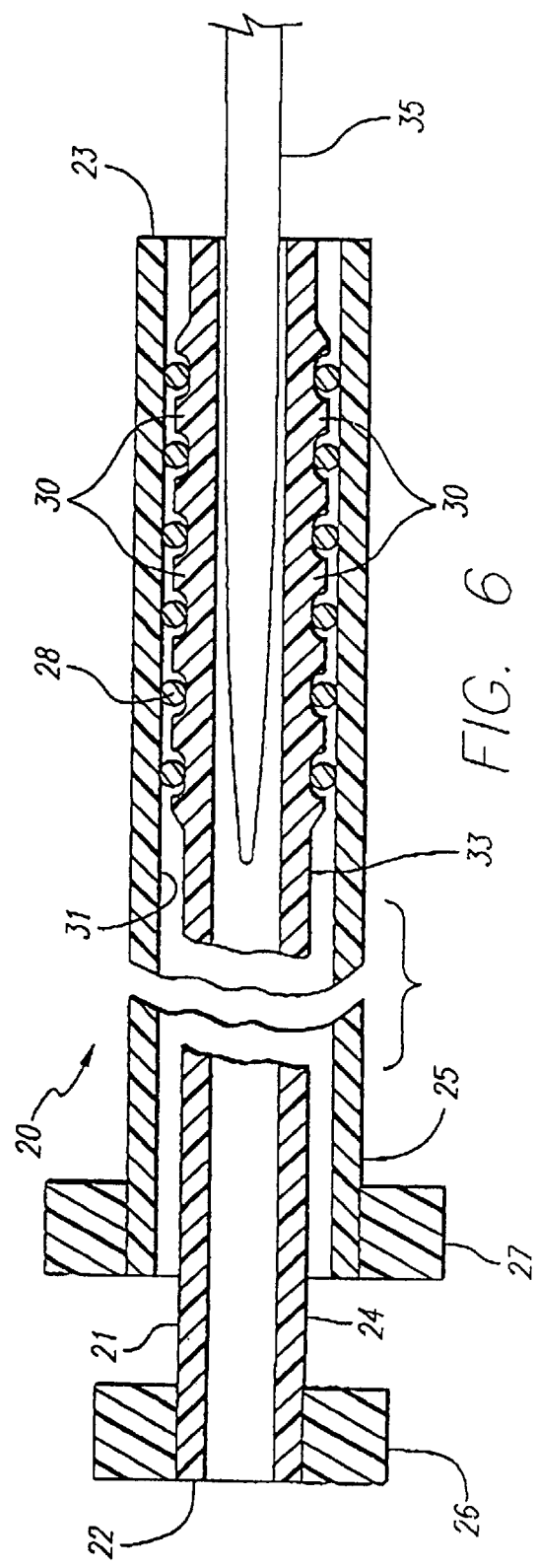

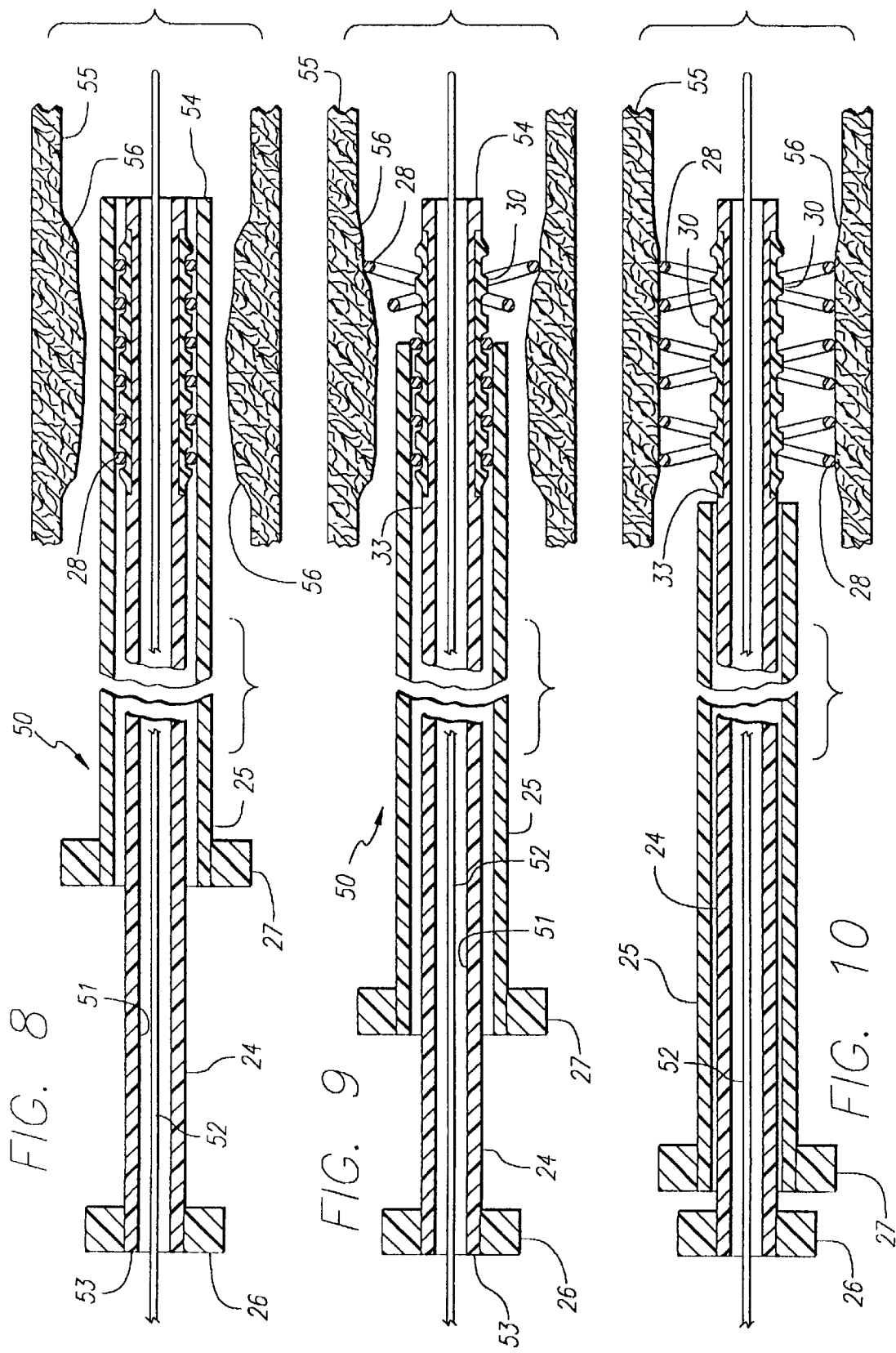

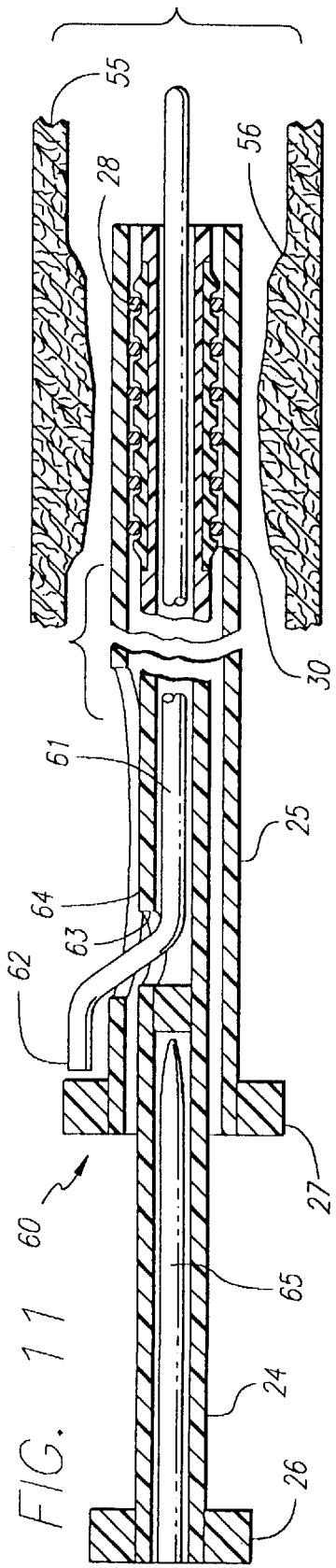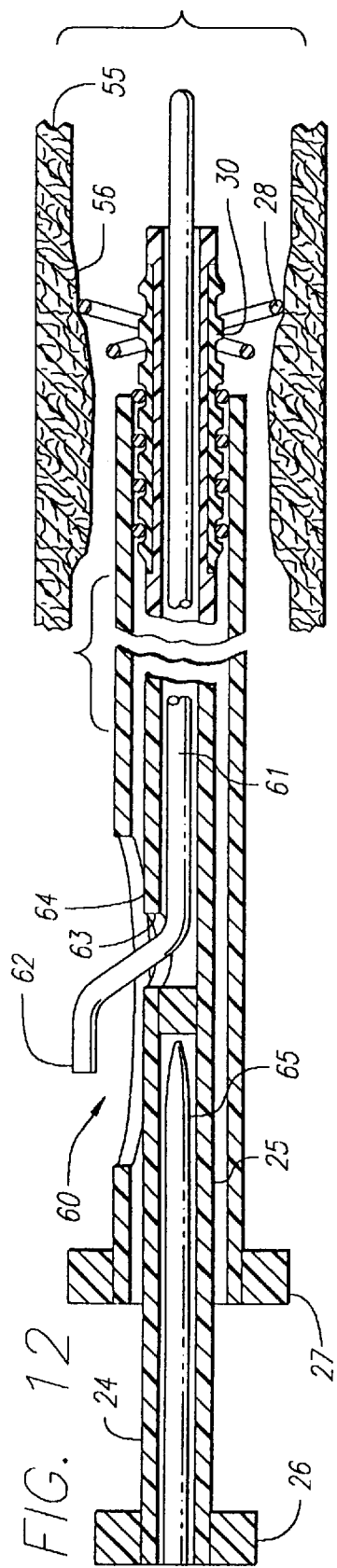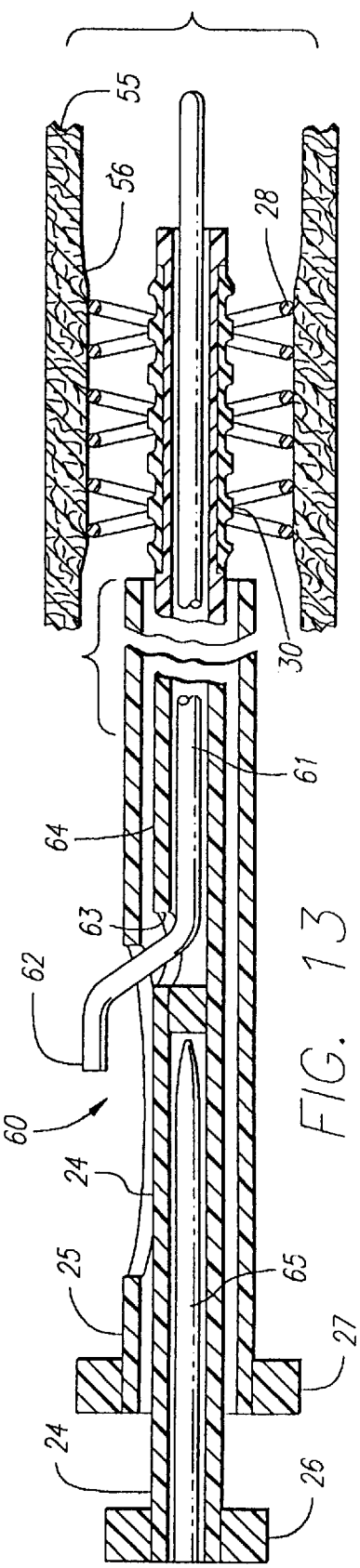

SELF-EXPANDING STENT DELIVERY SYSTEM

BACKGROUND OF THE INVENTION

The invention relates to self-expanding stent delivery systems, which are used to implant a stent into a patient's body lumen to maintain the patency thereof. The stent delivery system is useful in the treatment and repair of body lumens, including coronary arteries, renal arteries, carotid arteries, and other body lumens.

Stents are generally cylindrically-shaped devices which function to hold open and sometimes expand a segment of a blood vessel or other body lumen. They are particularly suitable for use to support and hold back a dissected arterial lining which can occlude the fluid passageway therethrough. Stents also are useful in maintaining the patency of a body lumen, such as a coronary artery, after a percutaneous transluminal coronary angioplasty (PTCA) procedure or an atherectomy procedure to open a stenosed area of the artery.

A variety of devices are known in the art for use as stents and have included coiled wires in a variety of patterns that are expanded after being placed intraluminally by a balloon catheter; helically wound coil springs manufactured from an expandable heat sensitive material such as nickel-titanium; and self-expanding stents inserted in a compressed state and shaped in a zig-zag pattern.

Typically, the aforementioned stents are delivered intraluminally through a percutaneous incision through the femoral or renal arteries. A stent is mounted on the distal end of an elongated catheter, typically on the balloon portion of a catheter, and the catheter and stent are advanced intraluminally to the site where the stent is to be implanted. Typically with expandable stents, the balloon portion of the catheter is inflated to expand the stent radially outwardly into contact with the arterial wall, whereupon the stent undergoes plastic deformation and remains in an expanded state to hold open and support the artery.

With respect to self-expanding stents, typically a retractably sheath is positioned over the self-expanding stent which is mounted on the distal end of the catheter. Once the catheter has been advanced intraluminally to the site where the stent is to be implanted, the sheath is withdrawn thereby allowing the self-expanding stent to expand radially outwardly into contact with the arterial wall, thereby holding open and supporting the artery.

One of the problems associated with the prior art stents and catheter-delivery systems, is to removably attach the stent to the catheter's distal end or the balloon portion of the catheter so that the stent does not dislodge or move axially on the catheter or balloon.

What has been needed and heretofore unavailable is a reliable catheter-delivery system on which the stent can be mounted and removably attached so that it does not move axially on the catheter either during delivery and advancement through the vascular system, or during implanting of the stent. The present invention satisfies this need.

SUMMARY OF THE INVENTION

The present invention is directed to a self-expanding stent delivery system in which a self-expanding stent is removably attached to a catheter so that the stent remains in position on the catheter until it is implanted. Unlike prior art stents, which may have a tendency to dislodge or move axially on the catheter shaft when the sheath is withdrawn or when the catheter is advanced through a tortuous vasculature, the present invention provides means for removably attaching the stent to the catheter so that it cannot move axially on the catheter shaft.

A catheter assembly for removably attaching an intravascular stent is provided in which an elongated catheter has an inner member and an outer member extending along a longitudinal axis wherein the inner member and the outer member have a coaxial configuration and are dimensioned for relative axial movement. A self-expanding stent, having an open lattice structure, and being biased toward an open configuration, is mounted within the outer member. The inner member is slidably positioned within the lumen of the stent, and then the inner member is heated until it conforms and fills the open lattice structure of the stent with attachment projections.

The present invention includes an inner member that is naturally pliable and deformable or is heat-deformable and formed from a polymeric material which when heated will fill the open lattice structure of the stent with attachment projections. The inner member can be formed from polymeric materials including polyurethanes, polyethylenes, polyethylterpthalate, and nylons.

In another embodiment of the invention, an elastomeric sleeve is attached to the distal end of the inner member. This stent is mounted in the distal end of the outer member and is biased outwardly against the outer member. The inner member distal end and its sleeve are positioned within the stent, and the sleeve is heated until it fills and forms attachment projections in the open lattice structure of the stent.

The invention also relates to the method of mounting the self-expanding stent on the delivery catheter. The delivery catheter includes an outer member and an inner member having relative axial movement and control handles for providing relative axial movement between the members. The self-expanding stent is positioned within the inner lumen of the outer member and the control handles are manipulated to slide the inner member distal end within the inner lumen of the self-expanding stent. Thereafter, heat is applied to the inner member distal end so that it conforms and fills the open lattice structure of the self-expanding stent with attachment projections, thereby removably attaching the self-expanding stent to the inner member distal end and preventing axial movement of the stent. The self-expanding stent remains biased radially outwardly and is retained from expanding by the outer member.

The invention also includes a method of implanting a self-expanding stent utilizing the catheter-delivery system described above. Using the catheter-delivery system, the stent is advanced through a patient's vascular system until it is positioned at the site where the stent is to be implanted. The control handles are manipulated to simultaneously move the inner member axially in a distal direction and the outer member axially in a proximal direction. As the stent is exposed and no longer retained by the outer member, it will deploy by self-expanding radially outwardly into contact with the body lumen. The stent will not move axially on the catheter shaft as the inner member and the outer member are moved axially relative to one another, since the stent is removably attached to the inner member by attachment projections. After the stent is deployed, the catheter-delivery system is withdrawn from the patient.

One feature of the present invention is to permit the physician to partially deploy the stent, and if it is improperly positioned, the outer member can be moved axially to recapture the partially deployed stent so that the stent can be repositioned in the proper location. For example, the control handles can be manipulated to simultaneously move the inner member axially in the distal direction and the outer member axially in a proximal direction to begin to deploy the stent. Thereafter, if it is determined that the stent is being implanted at the wrong location in an artery, the control handles can be manipulated to simultaneously move the inner member axially in a proximal direction and the outer member axially in a distal direction to recapture the partially deployed stent so that it can be repositioned in the proper location in the artery. The stent is then implanted as described above.

Other features and advantages of the present invention will become more apparent from the following detailed description of the invention, when taken in conjunction with the accompanying exemplary drawings.

BRIEF DESCRIPTION OF THE DRAWINGS

FIGS. 1–4 represent elevational views of prior art stents and catheter-delivery systems where the stents are self-expanding either because they are biased radially outwardly or formed from a heat sensitive material such as nickel-titanium.

FIG. 5 is a schematic view of the catheter-delivery system of the invention having the self-expanding stent positioned within the inner lumen of the outer member before the stent is mounted on the inner member.

FIG. 5A is a cross section of FIG. 5 along line 5A–5A.

FIG. 6 is a schematic view depicting the inner member positioned within the inner lumen of the self-expanding stent, and a tapered mandril inserted in the inner member for the purpose of applying heat to form attachment projections.

FIG. 8 is a schematic view of an over-the-wire catheter-delivery system in which the stent is being positioned at a narrowed portion of the vessel wall.

FIG. 9 is a schematic view depicting the over-the-wire catheter-delivery system of FIG. 8 in which the outer member is being withdrawn proximally so that the stent can self-expand radially outwardly into contact with the vessel wall.

FIG. 10 is a schematic view depicting the stent of FIGS. 8 and 9 being implanted and contacting the vessel wall.

FIG. 11 is a schematic view depicting a rapid-exchange catheter-delivery system in which the guide wire extends through a port in the side of catheter so that the catheter may be rapidly exchanged upon withdrawal from the patient.

FIG. 12 is a schematic view depicting the catheter-delivery system of FIG. 11 in which the stent is self-expanding as the outer member is withdrawn axially in the proximal direction.

FIG. 13 is a schematic view depicting the rapid-exchange catheter-delivery system in which the self-expanding stent has been implanted into contact with the vessel wall, and the rapid-exchange catheter is ready to be withdrawn from the patient's vascular system.

DETAILED DESCRIPTION OF THE PREFERRED EMBODIMENTS

Figure 1:
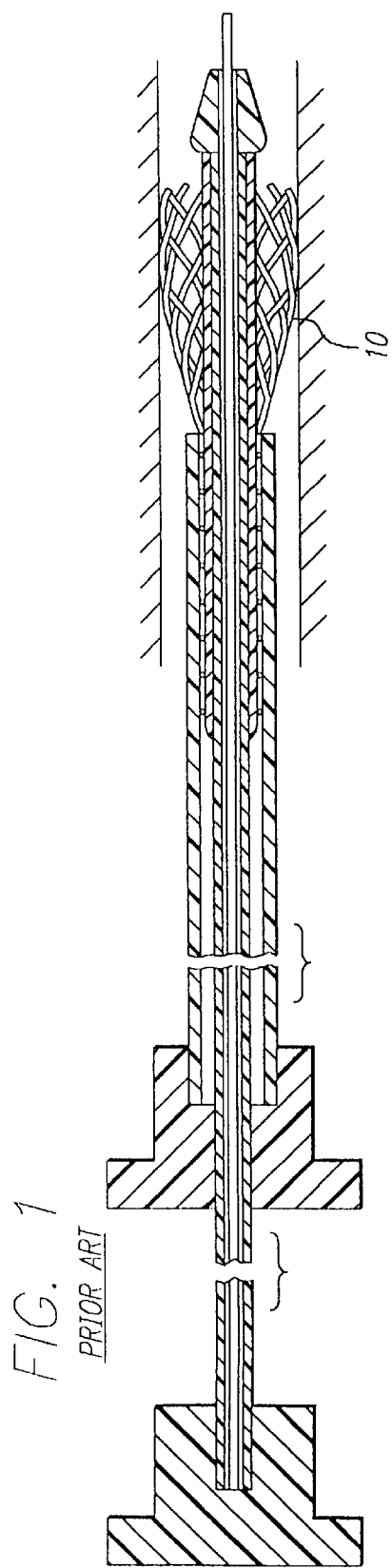
Figure 2:
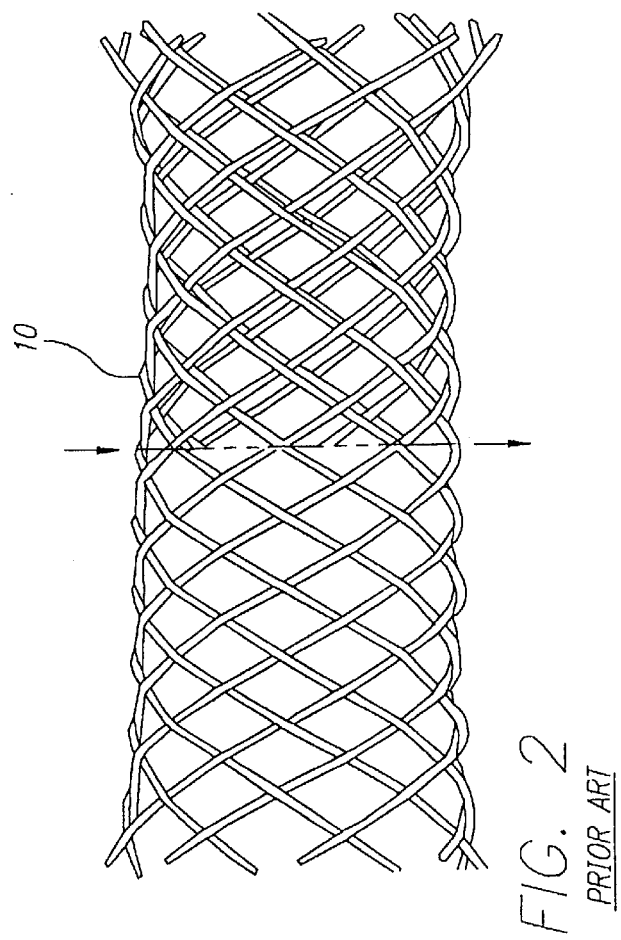

The present invention relates to a stent delivery catheter system in which a self-expanding stent is delivered intraluminally into a human patient's body lumen, such as a coronary artery, carotid artery, renal arteries, peripheral arteries and veins, and the like. The invention provides for a stent delivery catheter assembly and its method of use in which a stent is implanted in a patient.

As can be seen in FIGS. 1–4, there are numerous prior art stents which are adapted for use with the present invention. The stents depicted in FIGS. 1–4 are all self-expanding stents and will expand from a contracted condition where they are mounted on the catheter assembly, to an expanded condition where the stent comes in contact with the body lumen. The stents are self-expanding, which can be achieved by several means. As depicted in FIGS. 1–4, the prior art stents are formed from a stainless steel material and are configured so that they are biased radially outwardly and they will expand outwardly unless restrained. The stents depicted in FIGS. 1–4 also can be formed from a heat sensitive material, such as nickel titanium, which will self-expand radially outwardly upon application of a transformation temperature. These prior art stents are representative of a large number of stents which can be adapted for use with the present invention.

In a preferred embodiment of the invention, as depicted in FIGS. 5, 5A and 6, catheter assembly 20 is provided to deliver and implant a stent. Catheter assembly 20 incorporates elongated catheter body 21 which has proximal end 22 and distal end 23. An inner member 24 and an outer member 25 are arranged in coaxial alignment. Inner member 24 is slidably positioned within outer member 25 and relative axial movement between the two members is provided by inner member control handle 26 and outer member control handle 27. The control handles 26,27 can take numerous forms, but are depicted schematically for ease of illustration. As an example, however, control handles 26, 27 can take the form of a thumb-switch arrangement, a rotating-screw-type arrangement, or a ratcheting arrangement. Such control handle means are well known in prior art catheter-delivery systems.

A self-expanding stent 28 having an open lattice structure 29 is mounted on the distal end 23 of catheter assembly 20. Self-expanding stent 28 can take virtually any configuration that has an open lattice structure 29, as can be seen in the examples of the prior art stents shown in FIGS. 1–4.

In keeping with the invention, the self-expanding stent 28 is inserted in outer member inner lumen 31 and positioned at the outer member distal end. In those instances where self-expanding stent 28 is made from stainless steel or a similar material that is biased outwardly, stent 28 will be compressed and inserted into inner lumen 31. Thereafter, inner member distal end 32 is positioned within stent inner lumen 34 so that the inner member outer surface 33 can come into contact with the stent inner lumen 34.

In keeping with the preferred embodiment, inner member distal end 32 is made from a polymeric material that either is soft by design, or will become soft when heat is applied. The intent is to removably attach self-expanding stent 28 on outer surface 33 of inner member 24. Outer surface 33 will partially fill the open lattice structure 29 of stent 28 to form attachment projections 30 so that the stent cannot move in an axial direction along outer surface 33 of inner member 24.

In the preferred embodiment, self-expanding stent 28 is mounted on outer surface 33 at the inner member distal end 32 and the open lattice structure 29 is filled by attachment projections 30. Due to the coaxial arrangement between inner member 24 and outer member 25, the inner lumen 31 of outer member 25 covers self-expanding stent 28 and helps to retain the stent on the outer surface 33 of the inner member 24.

In order to conform outer surface 33 so that it conforms or fills the open lattice structure 29 of the self-expanding stent with attachment projections 30, heat can be applied by various methods. For example, a tapered mandrill 35, as depicted in FIG. 6, is inserted in inner member distal end 32 in region of the stent. Heat is then applied to outer member 25 by known means, such as by using a heated capture tube (not shown) surrounding outer member 25. The capture tube can be formed from teflon, glass, or the like and generally is warmed by using heated air. As outer member warms, inner member 33 is inserted within inner lumen 31 of outer member 25 allowing attachment projections 30 to flow and form around stent 28.

Figure 7:
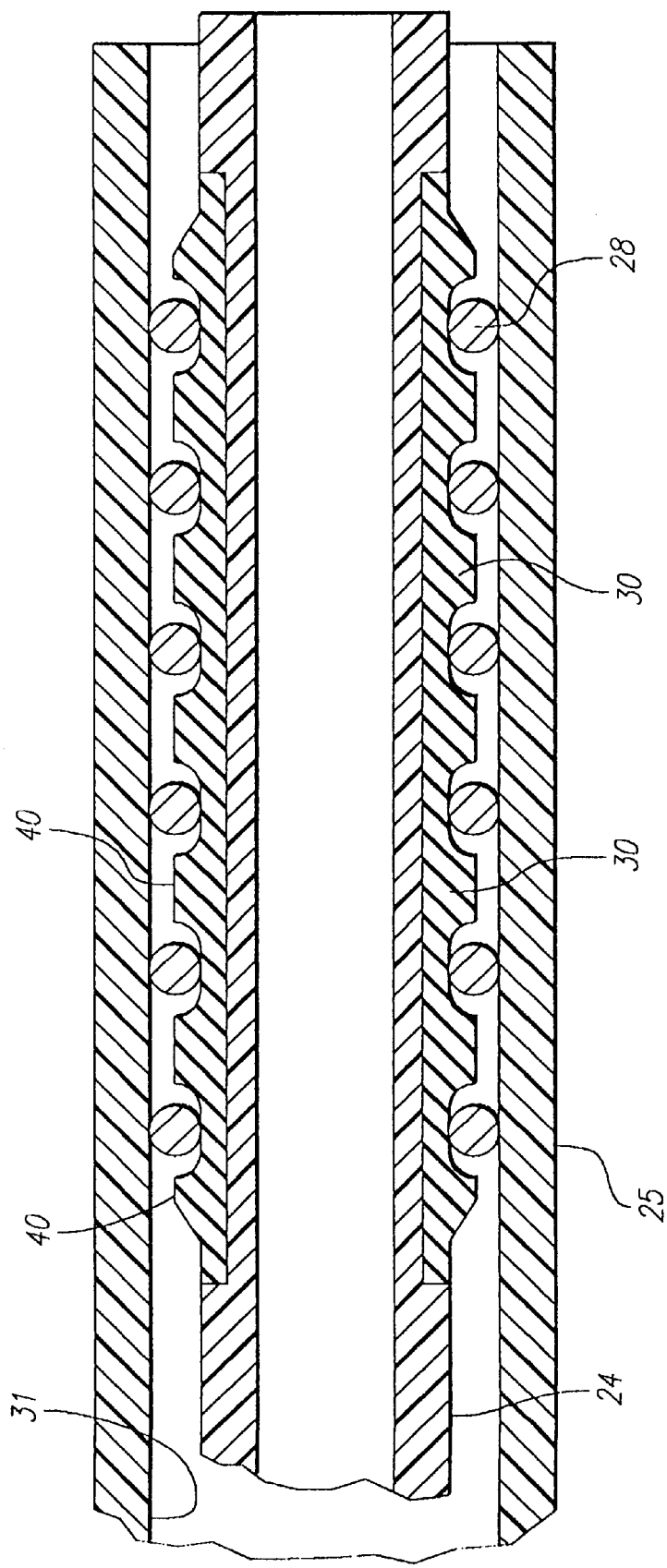
FIG. 7 is a schematic view depicting an alternative embodiment of the invention in which an elastomeric segment is positioned on the distal end of the inner member and is used to conform and fill in the open lattice structure of the self-expanding stent with attachment projections.

In another preferred embodiment, as depicted in FIG. 7, an elastomeric segment 40 is attached on outer surface 33 at the distal end 32 of the inner member. Elastomeric segment 40 is formed from a heat sensitive material, or is designed to be relatively soft as compared to inner member 24, such that stent 28 can be removably attached on elastomeric segment 40, which will conform and fill in open lattice structure 29 of the stent with attachment projections 30. The elastomeric segment can be heated by the aforementioned methods, or if it is formed of a material that is relatively soft, it will naturally conform and fill in open lattice structure 29 with attachment projections 30 without the application of heat.

In the preferred method of use, catheter assembly 20 is used to implant the self-expanding stent in a body lumen using an over-the-wire or rapid-exchange catheter configuration. In one preferred embodiment, as depicted in FIGS. 8–10, over-the-wire catheter 50 has a guide wire lumen 51 which extends through the catheter and is configured to receive guide wire 52. In order to implant self-expanding stent 28, guide wire 52 is positioned in a patient's body lumen, at vessel wall 55, and typically guide wire 52 extends past a stenosed region 56. Distal end 54 of over-the-wire catheter 50 is threaded over the proximal end of the guide wire which is outside the patient (not shown) and catheter 50 is advanced along the guide wire until distal end 54 of catheter 50 is positioned within stenosed region 56.

As depicted in FIGS. 9 and 10, self-expanding stent 28 is implanted in stenosed region 56 by moving outer member 25 in a proximal direction while simultaneously moving inner member 24 in a distal direction. The stent 28 will not slide or move axially on outer surface 33 since the open lattice structure is filled in with attachment projections 30. As portions of self-expanding stent 28 are no longer contained by outer member 24, it will expand radially outwardly into contact with vessel wall 55 in the area of stenosed region 56. When fully deployed and implanted, as shown in FIG. 10, stent 28 will support and hold open stenosed region 56 so that blood flow is not restricted. Attachment projections 30 do not inhibit the stent 28 from self-expanding radially outwardly, they only impede axial movement of the stent.

With certain self-expanding stents, there is a tendency of the stent to shorten somewhat when it expands. When stent shortening occurs, the physician may find that the stent has been improperly placed in the stenosed region 56 if the effects of shortening have not been taken into consideration. Accordingly, it may be necessary, as described above, to move inner member 24 distally in order to compensate for stent shortening upon expansion of the stent. It is also possible due to stent design, that the self-expanding stent will not appreciably shorten upon expansion. If this is the case, it may be unnecessary to move inner member 24 distally while simultaneously moving outer member 25 proximally in order to release self-expanding stent 28 in the body lumen. With a stent configuration that does not appreciably shorten during expansion, outer member 25 is moved axially while inner member 24 remains stationary as self-expanding stent 28 expands radially outwardly into contact with vessel wall 55. After stent 28 is implanted and contacts stenosed region 56, over-the-wire catheter 50 is withdrawn from the patient's vascular system. A typical over-the-wire catheter design is disclosed in U.S. Pat. No. B1 4,323,071, which is incorporated herein by reference.

In another preferred method of implanting a stent, as depicted in FIGS. 11–13, rapid-exchange catheter 60 is provided. Rapid-exchange catheters are known in the art and details of the construction and use are set forth in U.S. Pat. Nos. 5,458,613; 5,346,505; and 5,300,085, which are incorporated herein by reference. Generally, rapid-exchange catheters include guide wire lumen 61 which extends in the distal portion of the catheter from side port 63 to the distal end of the catheter. Guide wire 62 is inserted through guide port 63 and extends out the distal end of catheter 60 so that the distal end of the guide wire is positioned beyond stenosed region 56. The method of deploying self-expanding stent 28 using rapid-exchange catheter 60 is similar to that described for using over-the-wire catheter 50. One of the differences between the catheter-delivery systems includes slit 64 in rapid-exchange catheter 60 which extends from side port 63 to approximately just proximal of the area where stent 28 is mounted. After stent 28 is implanted in stenosed region 56, rapid-exchange catheter 60 is withdrawn from the patient's vascular system and guide wire 62 will peel through slit 64 making the exchange of one catheter for another a simple process. Typically, stiffening mandrill 65 is incorporated in the proximal region of rapid-exchange catheter 60 to enhance the pushability of the catheter through the patient's vascular system, and to improve the trackability of the catheter over the guide wire.

The stents as described herein can be formed from any number of materials, including metals, metal alloys and polymeric materials. Preferably, the stents are formed from metal alloys such as stainless steel, tantalum, or the so-called heat sensitive metal alloys such as nickel titanium (NiTi). Stents formed from stainless steel or similar alloys typically are designed, such as in a helical coil or the like, so that they are spring biased outwardly.

With respect to stents formed from shape-memory alloys such as NiTi (nickel-titanium alloy), the stent will remain passive in its martensitic state when it is kept at a temperature below the transition temperature. In this case, the transition temperature will be below normal body temperature, or about 98.6° F. When the NiTi stent is exposed to normal body temperature, it will immediately attempt to return to its austenitic state, and will rapidly expand radially outwardly to achieve its preformed state. Details relating to the properties of devices made from nickel-titanium can be found in "Shape-Memory Alloys," *Scientific American*, Vol. 281, pages 74–82 (November 1979), which is incorporated herein by reference.

With respect to all of the embodiments disclosed above, inner member 24, and for that matter outer member 25, can be formed from polymeric materials including polyurethanes, polyethylenes, polyethylterpthalate, and nylons. Similarly, elastomeric segment 40 can be formed from polyurethane, elastomeric polyesters and the like. Generally speaking, the more proximal portions of inner member 24 and outer member 25 will be formed of a polymeric material that is stiffer than the distal section so that the proximal section has sufficient pushability to advance through the patient's vascular system. On the other hand, the more distal portion of inner member 24 and outer member 25 can be formed of a more flexible material so that the distal portion of the catheter will remain flexible and track more easily over the guide wire.

Other modifications and improvements may be made without departing from the scope of the invention. For example, the various drawing figures depict several configurations of the stent including various sizes, which can be modified to suit a particular application without departing from the spirit and scope of the invention. Further, the configuration of the catheter assembly is a coaxial arrangement between the inner member and the outer member, which can be modified to other configurations without departing from the preferred invention.

What is claimed is:

1. A catheter assembly comprising:
    an elongated catheter having a proximal end and a distal end;
    the catheter having an inner member and an outer member extending along a longitudinal axis, the inner member and the outer member having a coaxial configuration and dimensioned for relative axial movement;
    means for providing relative axial movement between the inner member and the outer member;
    a self-expanding stent having an open lattice structure configured to be biased from a delivery configuration having a reduced cross section and a predetermined length to an open configuration with an enlarged cross section and being positioned within a distal end of the outer member in the delivery configuration; and
    a plurality of attachment projections at a distal end of the inner member spaced along the stent a distance at least as great as the predetermined length for facilitating the removable attachment of the stent to the inner member distal end.

2. The catheter assembly of claim 1, wherein the attachment projections are formed from a heat-deformable polymeric material at the distal end of the inner member.

3. The catheter assembly of claim 2, wherein the polymeric material on the distal end of the inner member is taken from the group of polymeric materials including polyurethanes, polyethylenes, polyethylterpthalate, and nylons.

4. The catheter assembly of claim 1, wherein the means for providing relative axial movement between the inner member and the outer member includes a control handle positioned at the proximal end of the elongated catheter.

5. The catheter assembly of claim 1, wherein the self-expanding stent is formed from a metal alloy taken from the group of metal alloys including stainless steel, nickel-titanium, and tantalum.

6. The catheter assembly of claim 1, wherein the inner member of the elongated catheter has a through lumen for receiving a guide wire so that the elongated catheter can be positioned within a body lumen by advancing it over the guide wire.

7. The catheter assembly of claim 1, wherein the inner member of the elongated catheter has a side port for receiving a guide wire, the side port being positioned so that the catheter can be rapidly exchanged.

8. The catheter assembly of claim 1, wherein the distal end of the elongated catheter includes an elastomeric sleeve attached to the distal end, the elastomeric sleeve adapted to conform and fill the lattice structure of the self-expanding stent with the plurality of attachment projections.

9. A method of mounting an intravascular stent on a delivery catheter, the method comprising:

providing a delivery catheter having an elongated catheter body and a proximal end and a distal end, the catheter having an inner member and an outer member extending along a longitudinal axis, the inner member and the outer member having a coaxial configuration and dimensioned for relative axial movement, and control handles for providing relative axial movement between the inner member and the outer member;

positioning a self-expanding stent in a delivery configuration having an open lattice structure a reduced cross section and a predetermined length within an inner lumen of the outer member;

manipulating the control handles to slide the inner member distal end within an inner lumen of the self-expanding stent; and heating the inner member distal end so that it conforms and fills the open lattice structure of the self-expanding stent with a plurality of attachment projections spaced along the stent a distance at least as great as the predetermined length thereby removably attaching the self-expanding stent to the inner member distal end.

10. A method of implanting a self-expanding stent in a body lumen, the method comprising:

providing an elongated catheter having a proximal end and a distal end, the catheter having an inner member and an outer member extending along a longitudinal axis, the inner member and the outer member having a coaxial configuration and dimensioned for relative axial movement, the inner member distal end encircled by a self-expanding stent in a delivery configuration having a reduced cross section and a predetermined length, the inner member capable of being heated whereby it conforms and fills an open lattice structure of the self-expanding stent with a plurality of attachment projections, the projections spaced along the stent a distance at least as great as the predetermined length, control handles for providing relative axial movement between the inner member and the outer member, and the distal end of the outer member forming a sheath around the self-expanding stent;

manipulating the control handles to simultaneously move the inner member axially in a distal direction and the outer member axially in a proximal direction;

deploying the stent by permitting it to self-expand radially outwardly into contact with the body lumen while preventing axial movement of the stent on the catheter by a plurality of the attachment projections; and withdrawing the catheter from the body lumen.

11. The method of implanting a stent of claim 10, the method further comprising the deploying and withdrawing steps further including:

positioning the distal end of the catheter at the site for implanting the stent;

manipulating the control handles to simultaneously move the inner member axially in a distal direction and the outer member axially in a proximal direction to begin implanting the stent;

manipulating the control handles to simultaneously move the inner member axially in a proximal direction and the outer member axially in a distal direction to recapture the stent and to position the stent on the inner member distal end;

repositioning the catheter distal end to implant the stent;

manipulating the control handles to simultaneously move the inner member axially in a distal direction and the outer member axially in the proximal direction to release the stent to self-expand in the body lumen; and withdrawing the catheter from the body lumen.

12. A method of implanting a self-expanding stent in a body lumen, the method comprising:

providing an elongated catheter having a proximal end and a distal end, the catheter having an inner member and an outer member extending along a longitudinal axis, the inner member and the outer member having a coaxial configuration and dimensioned for relative axial movement, the inner member distal end encircled by a self-expanding stent in a delivery configuration having an open lattice structure, a reduced cross section and a predetermined length, the inner member capable of being heated whereby it conforms and fills the open lattice structure of the self-expanding stent with a plurality of attachment projections, the projections spaced along the stent a distance at least as great as the predetermined length, control handles for providing relative axial movement between the inner member and the outer member, the distal end of the outer member forming a sheath around the self-expanding stent;

manipulating the control handles to move the outer member axially in a proximal direction while maintaining the inner member stationary;

deploying the stent by permitting it to self-expand radially outwardly into contact with the body lumen; and withdrawing the catheter from the body lumen.

13. The method of implanting a stent of claim 12, the method further comprising, prior to said withdrawing step:

positioning the distal end of the catheter at the site for implanting the stent;

manipulating the control handles to simultaneously move the inner member axially in a proximal direction and the outer member axially in a distal direction to recapture the stent;

repositioning the catheter distal end to implant the stent;

manipulating the control handles to move the outer member axially in the proximal direction to release the stent to self-expand in the body lumen while simultaneously holding the inner member stationary; and withdrawing the catheter from the body lumen.

* * * * *

UNITED STATES PATENT AND TRADEMARK OFFICE
CERTIFICATE OF CORRECTION

PATENT NO. : 6,077,295
DATED : June 20, 2000
INVENTOR(S) : Timothy A. Limon, Richard J. Saunders It is certified that error appears in the above-identified patent and that said Letters Patent is hereby corrected as shown below:

Column 5,
Line 4, change "mandrill", to read -- mandril --.
Line 48, change "24", to read -- 25 --.

Column 7,
Line 41, change "the", to read -- a --.
Line 49, change "the", to read -- a --.
Lines 62 and 63, change "elongated catheter includes an elastic sleeve attached to the distal end, the elastic sleeve", to read -- inner member includes an elastic sleeve --.

Signed and Sealed this

Fourteenth Day of August, 2001

*Attest:*

*Attesting Officer*

NICHOLAS P. GODICI
*Acting Director of the United States Patent and Trademark Office*